United States Patent
La Grone et al.

(10) Patent No.: US 8,647,579 B2
(45) Date of Patent: Feb. 11, 2014

(54) HYDROGEN PEROXIDE DETECTOR COMPRISING LIGHT-BLOCKING TIP WITH AIR DEFLECTOR

(75) Inventors: Marcus La Grone, Fairbanks, AK (US); Brian Dwayne O'Dell, Stillwater, OK (US); Robert Deans, Grafton, MA (US); Aimee Rose, Cambridge, MA (US)

(73) Assignee: Nomadics, Inc., Stillwater, OK (US)

( * ) Notice: Subject to any disclaimer, the term of this patent is extended or adjusted under 35 U.S.C. 154(b) by 719 days.

(21) Appl. No.: 12/531,920

(22) PCT Filed: Aug. 24, 2007

(86) PCT No.: PCT/US2007/018722
§ 371 (c)(1),
(2), (4) Date: Feb. 4, 2010

(87) PCT Pub. No.: WO2008/121124
PCT Pub. Date: Oct. 9, 2008

(65) Prior Publication Data
US 2010/0144050 A1    Jun. 10, 2010

Related U.S. Application Data

(60) Provisional application No. 60/918,809, filed on Mar. 19, 2007.

(51) Int. Cl.
*G01J 1/48*    (2006.01)
(52) U.S. Cl.
USPC .............. 422/86; 422/82.05; 422/83; 422/88
(58) Field of Classification Search
None
See application file for complete search history.

(56) References Cited

U.S. PATENT DOCUMENTS

| | | | |
|---|---|---|---|
| 3,749,679 A | 7/1973 | Rauhut |
| 3,816,325 A | 6/1974 | Rauhut et al. |
| 4,680,268 A | 7/1987 | Clark, Jr. |
| 4,765,961 A | 8/1988 | Schiff et al. |
| 5,043,851 A | 8/1991 | Kaplan |
| 5,092,220 A | 3/1992 | Rounbehler |
| 5,340,714 A | 8/1994 | Katsilometes |
| 5,348,690 A | 9/1994 | Cohen et al. |
| 5,380,650 A | 1/1995 | Barnard et al. |

(Continued)

FOREIGN PATENT DOCUMENTS

| | | |
|---|---|---|
| EP | 0228046 | 12/1986 |
| EP | 0745684 | 4/1996 |

(Continued)

OTHER PUBLICATIONS

Stigbrand et al. "1,1'-Oxalyldiimidazole as Chemiluminescence Reagent in the Determination of low Hydrogen Peroxide Concentrations by Flow Injection Analysis". vol. 66. pp. 1766-1770.*

(Continued)

*Primary Examiner* — Yelena G Gakh
(74) *Attorney, Agent, or Firm* — Wolf, Greenfield & Sacks, P.C.

(57) ABSTRACT

The current invention provides a detector and method suitable for sensing vapor-phase hydrogen peroxide. The detector utilizes a chemiluminescent material comprising a peroxide reactive compound, a dye and a solvent. Upon reaction with hydrogen peroxide, the chemiluminescent material will generate detectible light.

16 Claims, 5 Drawing Sheets

(56) References Cited

U.S. PATENT DOCUMENTS

| | | | |
|---|---|---|---|
| 5,389,302 | A | 2/1995 | Warren, Jr. |
| 5,434,084 | A | 7/1995 | Burgess, Jr. |
| RE35,007 | E | 8/1995 | Cohen et al. |
| 5,446,529 | A | 8/1995 | Stettner et al. |
| RE35,132 | E | 12/1995 | Bay et al. |
| D366,031 | S | 1/1996 | Bradbury |
| 5,488,544 | A | 1/1996 | Ladyjensky |
| 5,552,968 | A | 9/1996 | Ladyjensky |
| 5,566,679 | A | 10/1996 | Herriott |
| 5,582,170 | A | 12/1996 | Soller |
| 5,931,383 | A | 8/1999 | Palmer et al. |
| 5,980,055 | A | 11/1999 | Palmer et al. |
| 6,065,847 | A | 5/2000 | Palmer et al. |
| 6,106,129 | A | 8/2000 | Cranor et al. |
| 6,126,871 | A | 10/2000 | Cranor |
| 6,159,878 | A | 12/2000 | Marsh |
| 6,189,368 | B1 | 2/2001 | Ichida et al. |
| 6,245,576 | B1 | 6/2001 | Hiley |
| 6,267,914 | B1 | 7/2001 | Cranor |
| 6,330,464 | B1 | 12/2001 | Colvin, Jr. et al. |
| 6,379,969 | B1 | 4/2002 | Mauze et al. |
| 6,406,918 | B1 | 6/2002 | Bannister et al. |
| 6,461,543 | B2 | 10/2002 | Earl |
| 6,558,626 | B1 | 5/2003 | Aker et al. |
| 6,569,786 | B1 | 5/2003 | Marsh |
| 6,579,722 | B1 | 6/2003 | Collins et al. |
| 6,635,415 | B1 | 10/2003 | Bollinger et al. |
| 6,711,423 | B2 | 3/2004 | Colvin, Jr. |
| 6,716,637 | B2 | 4/2004 | Weckstrom |
| 6,758,572 | B2 | 7/2004 | Ladyjensky |
| 6,767,717 | B1 | 7/2004 | Itzhaky et al. |
| 6,832,392 | B2 | 12/2004 | Palmer et al. |
| 6,875,399 | B2 | 4/2005 | McVoy |
| 6,946,300 | B2 | 9/2005 | Nguyen et al. |
| 6,953,549 | B2 | 10/2005 | Hill et al. |
| 6,962,758 | B2 | 11/2005 | Chen et al. |
| 6,984,524 | B2 | 1/2006 | Nguyen et al. |
| 7,016,714 | B2 | 3/2006 | Colvin, Jr. |
| 7,141,677 | B2 | 11/2006 | Lee et al. |
| 7,289,836 | B2 | 10/2007 | Colvin, Jr. |
| 2004/0051867 | A1 | 3/2004 | Brestel et al. |
| 2004/0053421 | A1 | 3/2004 | Nguyen et al. |
| 2004/0114130 | A1 | 6/2004 | Nguyen et al. |
| 2004/0171098 | A1 | 9/2004 | Akhavan-Tafti et al. |
| 2006/0008841 | A1 | 1/2006 | Okada et al. |
| 2008/0108885 | A1 | 5/2008 | Colvin, Jr. |
| 2009/0298048 | A1 | 12/2009 | Smider et al. |

FOREIGN PATENT DOCUMENTS

| | | |
|---|---|---|
| EP | 1130382 | 5/2007 |
| GB | 2095401 | 9/1982 |
| WO | WO97/47958 | 12/1997 |
| WO | WO99/57222 | 11/1999 |
| WO | WO2005043125 | 5/2005 |
| WO | PCT/US07/019248 | 8/2007 |

OTHER PUBLICATIONS

Tsukagoshi et al. "Direct Detection of Biomolecules in a Capillary Electrophoresis-Chemiluminescence Detection System". 2004. Anal. Chem. vol. 76. pp. 4410-4415.*

D. Kietzmann et al., "Hydrogen peroxide in expired breath condensate of patients with acute respiratory failure and with ARDS", Intensive Care Med (1993) 19:78-81.

Allan L. Lazrus et al., "Automated Fluorometric Method for Hydrogen Peroxide in Air", Anal. Chem, 1988, 58, 694-597.

Bakaltcheva et al.; A fiber optic biosensor for multianalyte detection: importance of preventing fluorophore aggregation; Sensors and Actuators B 51 (1998) 46-51.

Buttigieg et al.; Characterization of the explosive triacetone troperoxide and detection by ion mobility spectrometry; Forensic Science International 135 (2003) 53-59.

Crowson et al.; Development of an LC/MS method for the trace analysis of hexamethylenetriperoxidediamine (HMTD); The Analyst 126 (2001) 1689-1693.

Dubnikova et al.; Novel Approach to the Detection of Triacetone Triperoxide (TATP): Its Structure and its Complexes with Ions; J. Phys. Chem. A 106 (2002) 4951-4956.

Kok et al.; Chemiluminescent Method for Determination of Hydrogen Peroxide in the Ambient Atmosphere; Environmental Science & Technology, vol. 12, No. 9, Sep. 1978, 1072-1076.

Oxley et al.; Training Dogs to Detect Triacetone Triperoxide (TATP); Proc. of SPIE vol. 5403 (2004) 350-353.

Robinson et al.; Luminol/H202 Chemiluminescence Detector for the Analysis of Nitric Oxide in Exhaled Breath; Analytical Chemistry, vol. 71, No. 22, Nov. 15, 1999, 5131-5136.

Schulte-Ladbeck et al.; A field test for the detection of peroxide-based explosives; The Analyst 127 (2002) 1152-1154.

Schulte-Ladbeck et al.; Determination of triacetonetroperoxide in ambient air; Analytica Chimica Acta 482 (2003) 183-188.

Schulte-Ladbeck et al.; Liquid Chromatography-Post-Column Photochemical Conversion and Electrochemical Detection for Determination of Peroxide-Based Explosives; Chromatographia Supplement vol. 57 (2003) S-61-S-65.

Schulte-Ladbeck et al.; Trace Analysis of Peroxide-Based Explosives; Analytical Chemistry, col. 75, No. 4, Feb. 15, 2003, 731-735.

Stambouli et al.; Headspace-GC/MS detection of TATP traces in post-explosion debris; Forensic Science International 146S (2004) S191-S194.

Todd et at.; Application of mid-infrared cavity-ringdown spectroscopy to trace explosives vapor detection using a broadly tunable (6-8um) optical parametric oscillator; Applied Physics B 75 (2002) 367-376.

Widmer et al.; Development of an LC/MS method for the trace analysis of triacetone triperoxide (TATP); The Analyst 127 (2002) 1627-1632.

Collins et al.; Chemiluminescent Chemical Sensors for Oxygen and Nitrogen Dioxide; Analytical Chemistry, vol. 67, No. 13, Jul. 1, 1995, 2224-2230.

Navas et al.; Air analysis: determination of hydrogen peroxide by chemiluminescence; Atmospheric Environment 33 (1999) 2279-2283.

Zhang et al.; Recent developments in chemiluminescence sensors; Trends in Analytical Chemistry, vol. 18, No. 6 (1999) 384-391.

Zhang et al.; Recent developments and applications of chemiluminescence sensors; Analytica Chimica Acta 541 (2005) 37-47.

Hool et al.; Immobilized Luminol Chemiluminescence Reagent System for Hydrogen Peroxide Determinations in Flowing Streams; Analytical Chemistry, vol. 60, No. 9, May 1, 1988, 834-837.

Janasek et al.; Novel chemiluminometric H202 sensors for the selective flow injection analysis; Sensors and Actuators B 51 (1998) 107-113.

Li et al.; Sol-gel horseradish peroxidase biosensor for the chemiluminescent flow determination of hydrogen peroxide; Anal. Commun., 36 (1999) 195-197.

Lin et al.; Hydrogen Peroxide chemiluminescent flow-through sensor based on the oxidation with periodate immobilized on ion-exchange resin; Microchemical Journal 69 (2001) 73-80.

Lobnik et al.; Sol-gel based optical sensor for continuous determination of dissolved hydrogen peroxide; Sensors and Actuators B 74 (2001) 194-199.

Omanovic et al.; A new chemiluminescence sensor for hydrogen peroxide determination; Intern. J. Environ. Anal. Chem. vol. 85, No. 12-13, Oct. 15-Nov. 15, 2005, 853-860.

Stigbrand et al.; 1,1'-Oxalyldilmidazole as Chemiluminescence Reagent in the Determination of Low Hydrogen Peroxide Concentrations by Flow Injection Analysis; Analytical Chemistry, vol. 66, No. 10, May 15, 1994, 1766-1770.

Shamsipur et al.; Effect of some aminoanthraquinone derivatives as red fluorescers on chemiluminescence systems originating from bis-(2,4,6-trichlorophenyl) oxalate and lucigenin; Journal of Photochemistry and Photobiology 174 (2005) 23-27.

(56) References Cited

OTHER PUBLICATIONS

Chokshi et al.; Oxalate/Hydrogen Peroxide Chemiluminescense Reaction. A F NMR Probe of the Reaction Mechanism; Biomedical Chromatography, vol. 4, No. 3 (1990) 96-99.

Yang et al.; Fluorescent Porous Polymer Films as TNT Chemosensors: Electronic and Structural Effects; J. Am. Chem. Soc. 120 (1998) 11864-11873.

Drager Safety AG & Co.; DragerSensor XS EC H202-68 09 170; Jul. 1, 2007 (2 pages).

Drager Safety AG & Co.; DragerSensor H202-68 09 675, Jul. 2005 (2 pages).

Honeywell; Manning EC-P2 A complete portable electrochemical datalogging gas leak detector; Sep. 2006; 4 pages.

Levitus, Marcia et al.; Polarized Electronic Spectroscopy and Photophysical Properties of 9,10-Bis (phenylethynul) anthracene; J. Phys. Chem. A 2000, 104, 8632-8637.

Navas, M.J. et al.; Air analysis: determination of hydrogen peroxide by chemiluminescence; Atmospheric Environment 33 (1999) 2279-2283.

He et al., "Turn on fluorescence sensing of vapor phase electron donating amines via tetraphenylporphyrin or metallophenhylporphrin doped polyfluorene," Chem. Commun., 2010, vol. 46, pp. 7536-7538.

* cited by examiner

HYDROGEN PEROXIDE DETECTOR COMPRISING LIGHT-BLOCKING TIP WITH AIR DEFLECTOR

CROSS REFERENCE TO RELATED APPLICATIONS

This Application is a national stage filing under 35 U.S.C. §371 of International Application No. PCT/US2007/018722, filed Aug. 24, 2007, which claims priority from U.S. Provisional Application Ser. No. 60/918,809, filed Mar. 19, 2007. The contents of each of these applications are incorporated herein by reference in their entireties for all purposes.

BACKGROUND OF THE INVENTION

This application incorporates by reference co-pending application filed on Apr. 5, 2007, entitled "Detection of Explosives and Other Species" and identified by Ser. No. 11/784,208.

The present invention is directed to the detection of peroxide compounds. In particular, the present invention provides a device suitable for detecting vapor-phase hydrogen peroxide and a method for using the same.

The majority of explosives detectors are design to monitor for nitrogen containing compounds such as TNT and dynamite. However, recent history has demonstrated that nitrogen based compounds are not the only materials suitable for creating explosives. In particular, terrorist organizations are known to have used peroxide compounds in the creation of bombs.

Existing explosives detectors either do not have the capability of detecting vapor-phase hydrogen peroxide or do not provide the portability necessary for use in areas where explosives based on peroxide compounds will likely be deployed. Additionally, standard testing procedures for determining the presence of peroxide compounds require excessive periods of time or lack the sensitivity necessary for use in airport security. Thus, there is a need for a portable explosives detector capable of detecting vapor-phase hydrogen peroxide in a very short period of time following exposure to vapor-phase hydrogen peroxide.

SUMMARY OF THE INVENTION

The current invention provides an apparatus suitable for detecting vapor-phase hydrogen peroxide. The apparatus comprises a housing assembly with a passageway therethrough. The passageway has an inlet and an outlet to permit passage of a flowing gas. The inlet carries a tip which reduces and preferably precludes entry of ambient light into the passageway. Preferably, the tip is heated. Positioned within the housing and in fluid communication with the passageway is a pump suitable for drawing gases from the exterior of the housing through the tip into the passageway. Also positioned within the housing is a sensor assembly. The sensor assembly is in fluid communication with the passageway and receives the flowing gas. The sensor assembly includes an optical detector and a liquid chemiluminescent compound carried by a solid support with the support defining or located within a reaction zone. Additionally, the sensor assembly preferably includes a heat source suitable to maintain the sensor assembly at an optimum operating temperature. The sensor assembly optionally includes a fan for this same purpose. The optical detector is positioned in a manner suitable for detecting light generated by the chemiluminescent material.

The current invention also provides a method for detecting hydrogen peroxide in the vapor-phase. In the method of the current invention, a sample of air or other gas suspected of carrying vapor-phase hydrogen peroxide is passed or pulled into an apparatus such as described above. After passing through a heated tip, the sample enters a passageway in the apparatus. The vapor-phase hydrogen peroxide subsequently contacts a chemiluminescent material positioned within the apparatus. Upon contact, the hydrogen peroxide reacts with the chemiluminescent material producing light. Detection of light by an optical detector positioned within the apparatus signals a positive test for hydrogen peroxide. Preferably, the reaction of the hydrogen peroxide with the chemiluminescent material occurs rapidly, i.e. within less than 10 seconds. Additionally, the chemiluminescent material preferably returns to the non-reactive state in less than 10 seconds after the exposure to the hydrogen peroxide vapor has ceased.

DETAILED DISCLOSURE OF THE PREFERRED EMBODIMENTS

I. Apparatus for Detecting Hydrogen Peroxide

Figure 1:
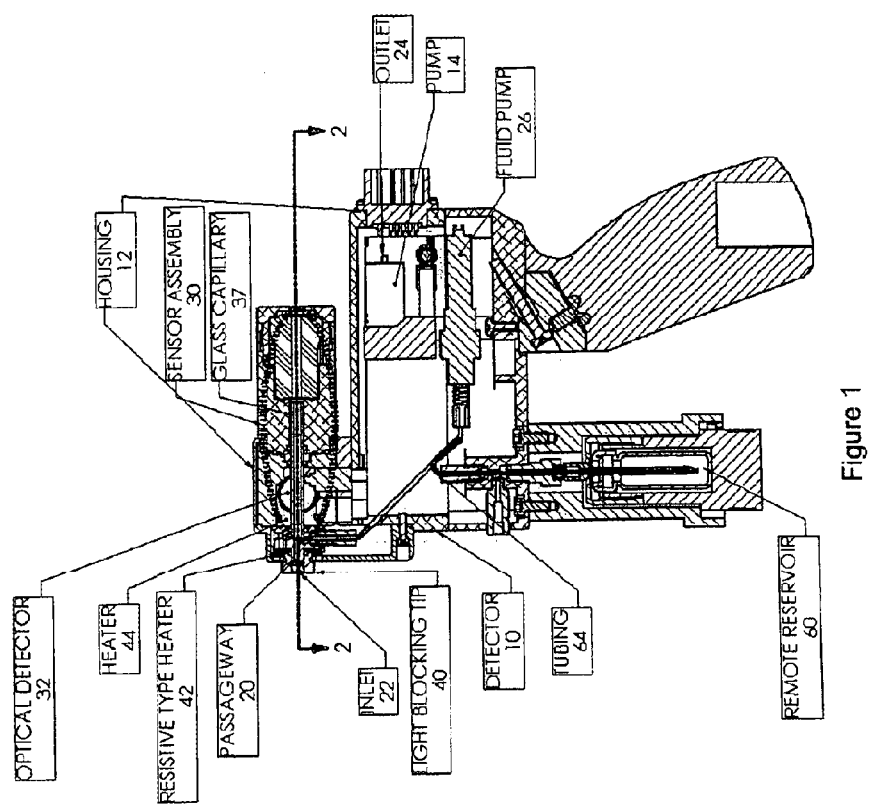
FIG. 1 is a sectional view of the detector of the current invention.
Figure 2:
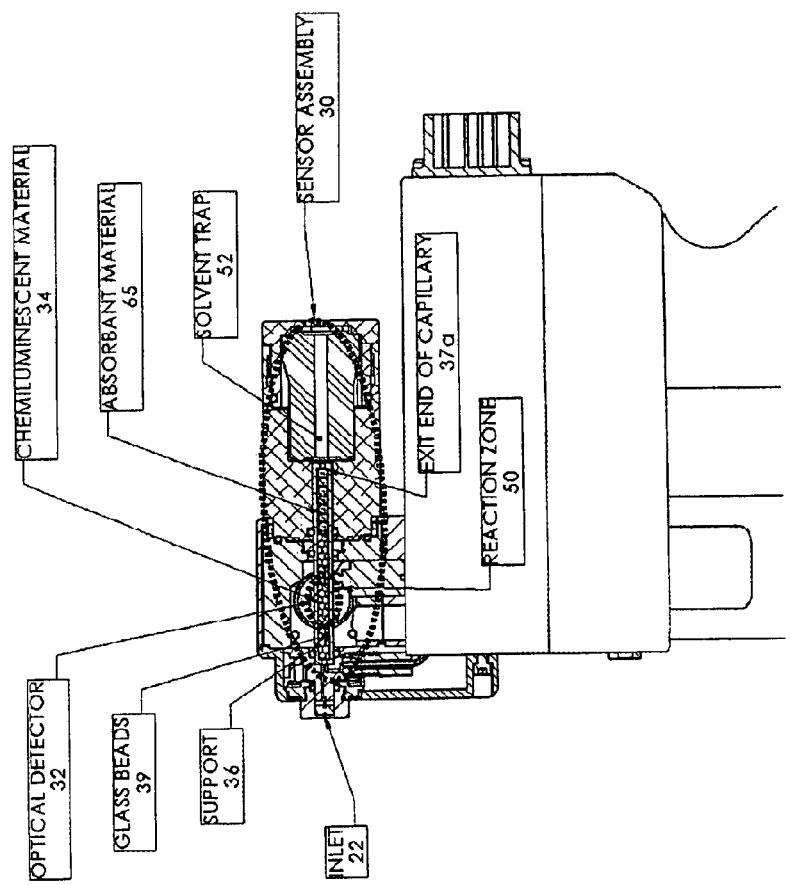
FIG. 2 is a sectional view of the sensor assembly housed within the detector depicting beads within the capillary.

In a preferred embodiment, the current invention provides a detector 10 suitable for determining the presence of vapor-phase hydrogen peroxide. Preferably, detector 10 is a hand held device suitable for screening high volumes of people and containers.

The apparatus of the current invention is similar in appearance to the apparatus disclosed in U.S. Pat. No. 6,558,626 which is incorporated herein by reference. While the device of the '626 patent is directed to the detection of nitrogen based compounds, the present invention provides a novel detector and sensor assembly suitable for the detection of hydrogen peroxide without any pretreatment of the hydrogen peroxide.

In a preferred embodiment, detector 10 comprises a housing 12, a pump 14 and a passageway 20, having an inlet 22 and an outlet 24, passing through detector 10. Pump 14, associated with passageway 20, provides for the movement of gases from the exterior of detector 10 through passageway 20. Pump 14 may be an inline pump positioned within passageway 20 or otherwise positioned in suitable fluid communication with passageway 20 to provide flow of a gas sample suspected of containing vapor-phase hydrogen peroxide through detector 10. Preferably, an in-line flow meter (not shown) monitors gas flow through detector 10 and communicates with a microprocessor or other suitable device. Thus, the in-line flow meter ensures a consistent flow of gas through detector 10 by controlling operation of pump 14.

Detector 10 further includes a sensor assembly 30 in fluid communication with passageway 20. Sensor assembly 30 includes an optical detector 32, a chemiluminescent material 34 carried by support 36 positioned in or defining reaction zone 50 and a carbon trap 52. Chemiluminescent material 34 is selected for its ability to produce light when reacted with hydrogen peroxide. In the preferred embodiment, sensor assembly 30 is positioned in fluid communication with passageway 20 such that gases pass over chemiluminescent material 34. Optical detector 32 is positioned adjacent to support 36 thereby permitting detection of light generated as a result of the reaction between hydrogen peroxide and chemiluminescent material 34. In the preferred embodiment, optical detector 32 is a photodiode. Optical detector 32 is preferably positioned out of the flow of gases passing through sensor assembly 30. Carbon trap, also known as solvent trap 52 is positioned downstream of reaction zone 50. Solvent trap 52 precludes the loss of solvent from chemiluminescent material 34 to pump 14 and the atmosphere. Finally, suitable electronics, software and displays for measuring and communicating a positive reaction detected by optical detector 32 are well known to those skilled in the art and will not be discussed herein.

In a preferred embodiment depicted in FIG. 1, detector 10 stores chemiluminescent material 34 in a remote reservoir 60. A fluid pump 26 and associated tubing 64 provide for movement of chemiluminescent material 34 from reservoir 60 to support 36. Preferably, remote reservoir 60 is a silanized glass vial.

To preclude or at least reduce the likelihood of a false positive by optical detector 32, a light blocking tip 40 is carried by detector 10. Light blocking tip 40 provides several functions in the current invention. As a primary function, tip 40 substantially reduces and preferably precludes the entry of ambient light into the area of detector 10 occupied by sensor assembly 30. More preferably, ambient light is precluded from entering reaction zone 50. Additionally, tip 40 enhances the gathering of gas for sampling by detector 10. Thus, hand held detector 10 is particularly suited for examining carry-on luggage and individuals at venues such as airports and sporting events.

Figure 3:
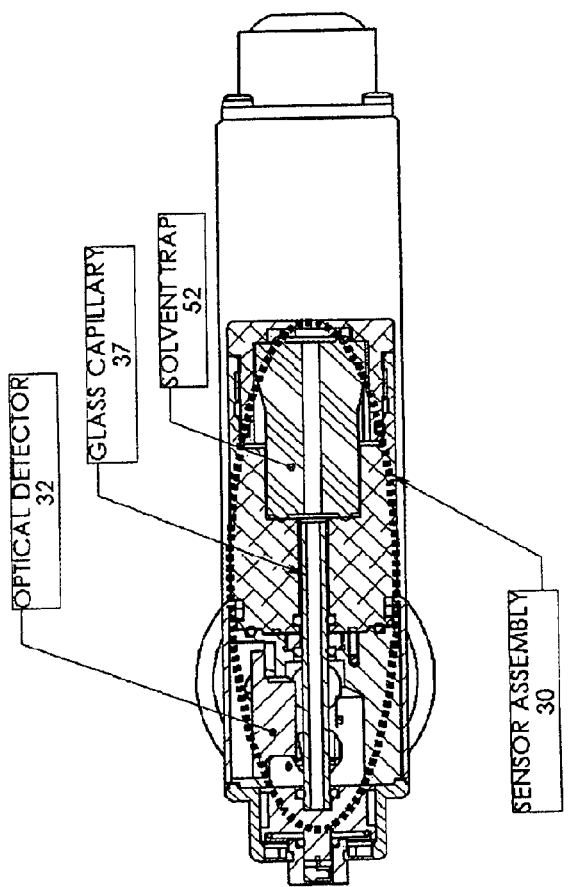
FIG. 3 is a top sectional view of the sensor assembly.
Figure 4:
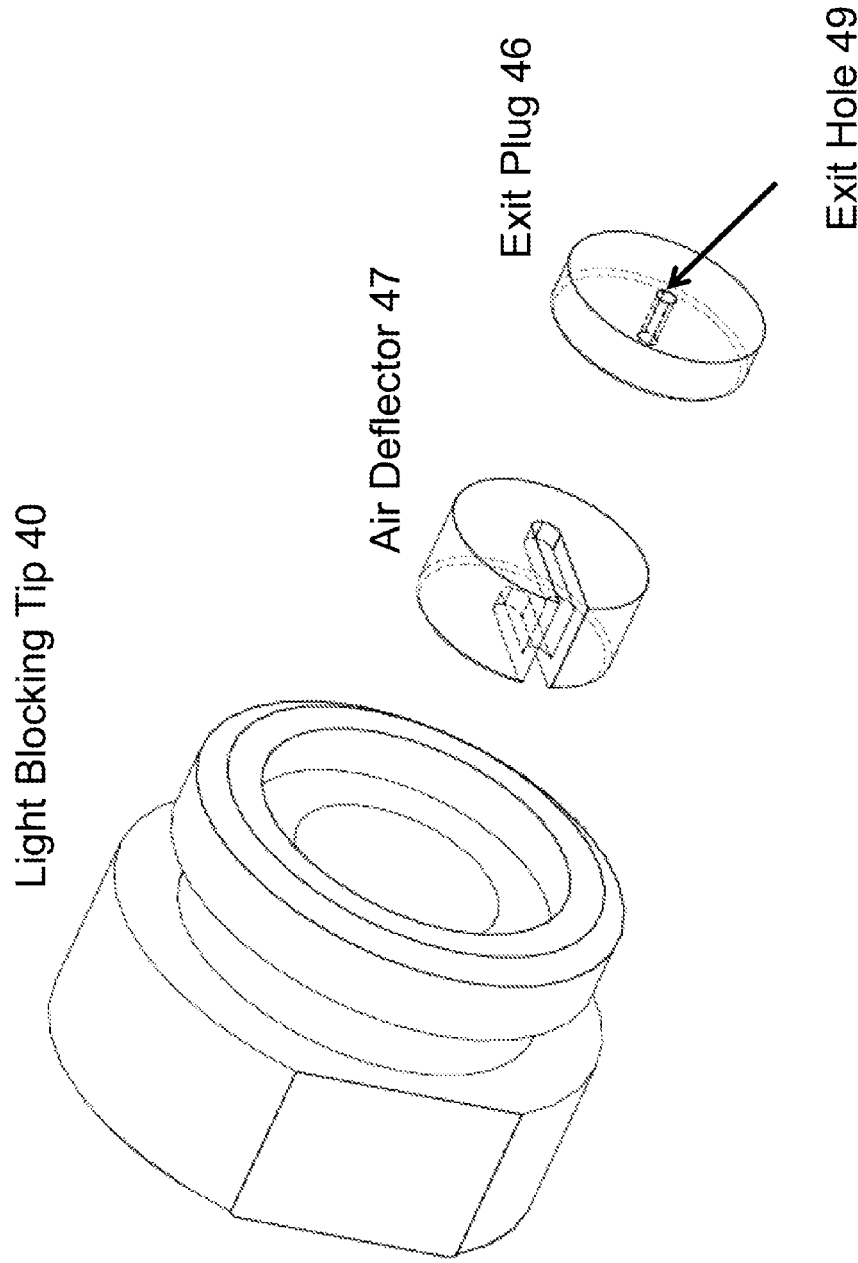
FIG. 4 is an explode view of the components of tip carried by the detector of the current invention.
Figure 5:
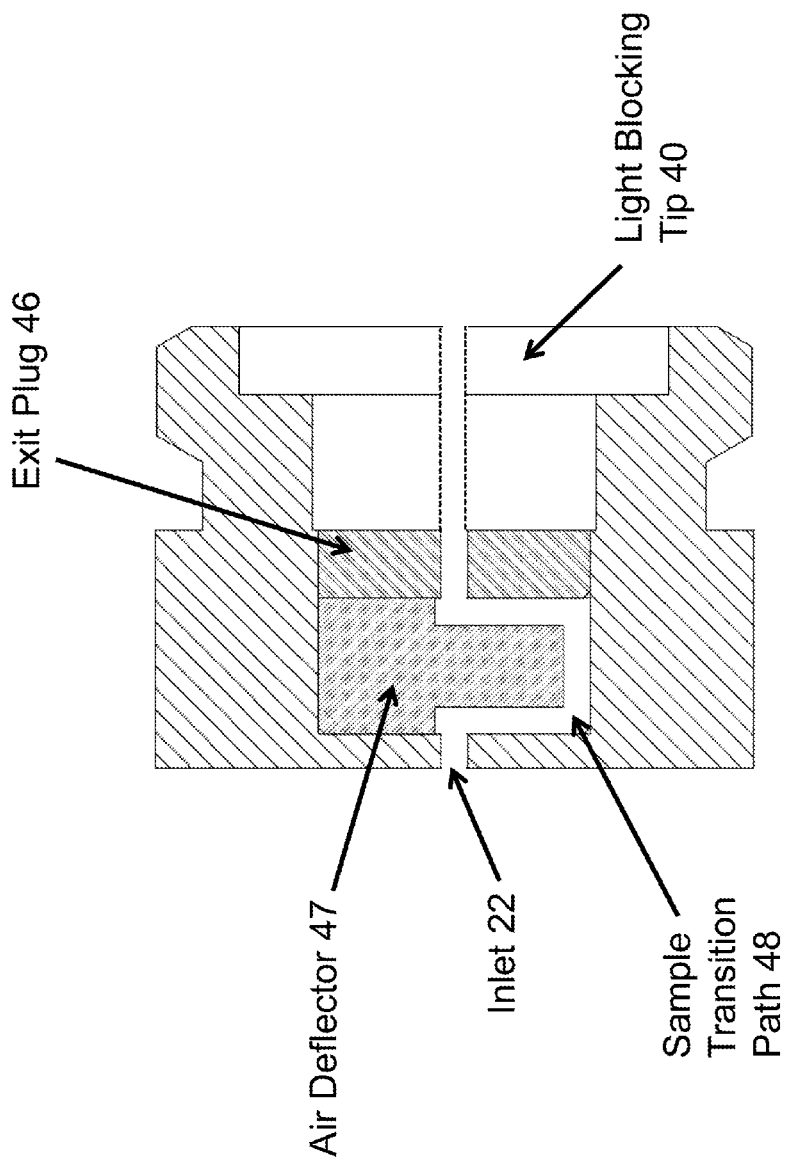
FIG. 5 is a sectional view of the tip carried by the detector of the current invention.

In the preferred embodiment, tip 40 includes inlet 22. As noted above, inlet 22 is in fluid communication with passageway 20. Tip 40 includes inner transition piece 47 and back piece 46 which cooperate to force sample gas entering detector through four 90° turns. Thus, the configuration of tip 40 substantially precludes penetration of ambient light to sensor assembly 30 without inhibiting gas sample flow. As depicted in FIGS. 3-5, gas passes through inlet 22 and encounters inner transition piece 47 which includes machined passages 48 defining the sample transition path through tip 40. Gas subsequently passes through exit hole 49 found in back piece 46 and enters capillary 37. Fluid connection provided from capillary 37 to outlet 22 is not shown. Tip 40, inner transition piece 47 and back piece 46 are preferably prepared from stainless steel which has been treated to substantially render tip components inert to peroxide. A preferred treatment utilizes Restek's Sulfinert® or Siltek® coatings.

The reaction rate of hydrogen peroxide and chemiluminescent material 34 can be improved by heating the gases prior to entering sensor assembly 30 and contacting chemiluminescent material 34. Additionally, heating of tip 40 is believed to preclude binding of peroxide molecules to tip 40 thereby further enhancing the sensitivity of detector 10. Therefore, in a preferred embodiment, tip 40 is heated either directly or indirectly. Typically, a resistive type heater 42 is positioned adjacent to tip 40 such that the temperature of tip 40 is between about 25° C. and about 100° C. Preferably, tip 40 is maintained at a temperature of about 65° C. In general, the preferred temperature of tip 40 is determined by the composition of chemiluminescent material 34.

Further, the preferred embodiment includes a heater 44 suitable for maintaining the temperature of the reaction zone 50 in the range of about 25° C. to about 150° C. Preferably, the temperature of reaction zone 50 will be about 55° C. However, the preferred temperature of reaction zone 50 will vary with the selection of chemiluminescent material 34. In general, the preferred temperature for reaction zone 50 is that temperature which provides the fastest reaction rate between hydrogen peroxide and chemiluminescent material 34. In an alternative embodiment, a single heater 42 is used to maintain the temperature of tip 40 and reaction zone 50.

Optionally, detector 10 includes a fan or other suitable cooling device (not shown). The fan provides the ability to maintain reaction zone 50 in the desired temperature range when detector 10 is used in high temperature environments.

In the preferred embodiment, chemiluminescent material 34 is carried by support 36. Support 36 may take several different forms provided that support 36 is non-reactive with and non-degraded by chemiluminescent material 34. Optionally, support 36 may be treated with silane and/or acid to improve shelf operational life of chemiluminescent material 34. See for example U.S. Pat. No. 3,974,368 incorporated herein by reference. The primary limitation on support 36 is to ensure that chemiluminescent material 34 has sufficient surface area to promote reaction with hydrogen peroxide while supporting chemiluminescent material 34 as a homogeneous and stable solution or dispersion.

One suitable support 36 is a transparent glass tube or capillary 37, which may be chemically etched to improve adhesion of the chemiluminescent material 34. Preferably, capillary 37 is positioned within an aluminum tube 41 within sensor assembly 30. Aluminum tube 41 has a slot running along at least a portion of its length to permit transmission of light from capillary 37 to optical detector 32. Preferably, aluminum tube 41 is attached to heater 42 by a thermocouple (not shown). A controller (not shown) supplies power to heater 42 and maintains the thermocouple at the desired setting. Optionally, a separate thermocouple or thermistor (not shown) associated with sensor assembly 30 monitors its temperature and compensates for thermal drift.

When support 36 is glass capillary 37, chemiluminescent material 34 is preferably spun coated on the interior of capillary 37 in a liquid form. Preferably, capillary 37 has a length of about 4.5 cm to about 7.5 cm and an internal diameter of 3 mm. However, the size of tube 37 is not considered to be limiting on the current invention with sizes ranging from traditionally capillary size to larger diameters suitable for use in stationary devices. Suitable glass capillaries may be prepared from quartz, borosilicate, soda lime glass, flint glass and other similar naturally occurring and synthetic materials. Optionally, a portion of capillary 37 beyond optical detector 32 may contain or be coated with an absorbent material 65 which serves to capture excess chemiluminescent material 34.

In the handheld device depicted in FIG. 1, support 36 is a capillary 37 carrying a sufficient layer (not shown) of chemiluminescent material 34 to react with vapor-phase hydrogen peroxide and generate detectible light. Preferably the layer of chemiluminescent material 34 is between about 2 μm and about 10 μm thick. Generally, capillary 37 contains about 2 μL of spun coated chemiluminescent material 34. Thus, in this embodiment, the interior of capillary 37 defines the area of reaction zone 50.

In a preferred embodiment, support 36 takes the form of glass beads 39 coated with chemiluminescent material 34 and positioned within glass capillary 37 which is also coated with chemiluminescent material 34. Coated beads 39 are retained within capillary 37 in a manner which readily permits passage of gases. For example, a short piece of plastic tubing (not shown) sized to fit within capillary 37 but having an inner diameter smaller than beads 39 will suffice. In general any material which permits passage of gas without reacting therewith will be suitable in the current invention. In this embodiment, glass capillary 37 is transparent to the light produced by chemiluminescent material 34 thereby permitting detection by optical detector 32. As in the previously described embodiment, the interior of capillary 37 defines the area of reaction zone 50. Preferably, capillary 37 has a length of about 4.5 cm to about 7.5 cm and an internal diameter of 3 mm. Suitable glass capillaries may be prepared from quartz, borosilicate, soda lime glass, flint glass and other similar naturally occurring and synthetic materials.

The addition of beads 39 to capillary 37 increases the effective surface area of support 36 thereby allowing an increased volume of chemiluminescent material 34 with reaction zone 50. The volume of chemiluminescent material 34 carried by beads 39 is sufficient to generate detectible light when exposed to vapor-phase hydrogen peroxide. Typically, the amount of chemiluminescent material 34 will be from about 40 µL to about 60 µL. Preferably, beads 39 and capillary 37 contain about 50 µL of chemiluminescent material 34. Thus, in this embodiment, the interior of capillary 37 and the surface of the beads 39 defines the area of reaction zone 50.

In a modification of this preferred embodiment, the capillary and beads may be heat treated, i.e. sintered, to mechanically fuse the beads to the capillary. The capillary, beads, or fused bead configuration are optionally treated to improve surface adhesion prolong the chemiluminescent material lifetime. For example, silane treatments, and/or acid etching of the glass walls are known to enhance the adhesion of polymers to the walls of glass beads and capillaries.

The preferred embodiment of detector 10 includes a remote reservoir 60. Provision of remote reservoir 60 removes the need to precoat capillary 37 and beads 39 with chemiluminescent material 34. Rather, reaction zone 50 is "primed" with chemiluminescent material 34 prior to the first use of detector 10 by initially pumping about 2 µL to about 30 µL of chemiluminescent material 34 into capillary 37. More preferably, 20 µL are initially provided to capillary 37 and beads 39. Preferably, remote reservoir 60 has sufficient volume to permit operation of detector 10 for at least an eight hour period when about 1 µL to about 4 µL of chemiluminescent material 34 is provided to capillary 37 about every fifteen minutes.

As noted above, optical detector 32 is preferably positioned out of the flow of gases through sensor assembly 30. In one embodiment, optical detector 32 is located at the exit end 37a of capillary 37 and is protected from the flow of gases by a transparent material, such as glass. More preferably, optical detector 32 is positioned to the side of reaction zone 50 out of the analyte flow path. This preferred location provides the advantage of positioning optical detector in close proximity to reaction zone 50 thereby increasing the percentage of generated light reaching optical detector 32, i.e. this position improves the collection efficiency of optical detector 32.

Other supports 36 such as slides and tapes, not shown, coated with chemiluminescent material 34 will also provide satisfactory results in the current invention. The primary limitation being the ability to provide sufficient surface area for the reaction between hydrogen peroxide and chemiluminescent material 34 in reaction zone 50 suitable for detecting the resulting light emission by optical detector 32.

Regardless of the type of support selected for chemiluminescent material 34, the preferred support will permit easy replacement of chemiluminescent material 34 and support 36. Thus, a removable capillary 37 having the interior either coated with chemiluminescent material 34 or housing beads 39 coated with chemiluminescent material 34 is particularly suited for the current invention.

Chemiluminescent material 34 can be any chemical compound or blend of chemical compounds in a liquid form which, when reacted with hydrogen peroxide, emit light. Alternatively, chemiluminescent material 34 can be any chemical compound or blend of chemical compounds which exist in solid form at room temperature but which liquefy at the system's operating temperatures and which emit light when reacted with hydrogen peroxide. Typically, chemiluminescent material 34 will produce light having an emission spectrum between 330-1200 nm when reacted with hydrogen peroxide. Preferably, the emission spectrum is between 400-700 nm. Light-emitting materials are known in the art and are described in "Fluorescence and Phosphorescence," by Peter Pringsheim, Interscience Publishers, Inc., New York, N.Y., 1949, and "The Color Index," Second Edition, Volume 2, The American Association of Textile Chemists and Colorists, 1956.

Additional light-emitting compounds are disclosed by U.S. Pat. Nos. 3,749,679 and 6,126,871 incorporated herein by reference. Commercially available compounds such as luminol (5-amino-2,3-dihydrophthalazine-1,4-dione or 3-aminophthalhydrazide) and Cyalume® (containing diphenylethandioate, a dye, and other components) will react with hydrogen peroxide to produce a photon of light in the visible spectrum. Other examples of peroxide-reactive materials include: 2,4,5-triphenylimidazole (lophine), 10,10'-dialkyl-9,9'-biacridinium salts (lucigenin), and 9-chlorocarbonyl-10-methylacridinium chloride (rosigenin).

In general, the peroxide reactive compound of chemiluminescent material 34 is a compound having the formula:

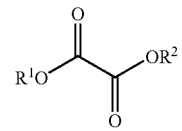

Wherein $R^1$ and $R^2$ are independently aryl, substituted aryl, heteroaryl, or substituted aryl. In some embodiments, the aryl or heteroaryl group may be substituted with hydrogen, hydroxy, halide, a carbonyl group, an optionally substituted amine, optionally substituted alkyl, optionally substituted alkoxy, cyano, and/or nitro group.

Oxalates suitable for use in the current invention include, but are not limited to, bis(2-nitrophenyl) oxalate, bis(2,4-dinitrophenyl) oxalate, bis(2,6-dichloro-4-nitrophenyl) oxalate, bis(2,4,6-trichlorophenyl) oxalate, bis(3-trifluoromethyl-4-nitrophenyl) oxalate, bis(2-methyl 4,6-dinitrophenyl) oxalate, bis(1,2-dimethyl-4,6-dinitrophenyl) oxalate, bis(2,4-dichlorophenyl) oxalate, bis(2,5-dinitrophenyl) oxalate, bis(2-formyl-4-nitrophenyl) oxalate, bis(pentachlorophenyl) oxalate, bis(pentafluorophenyl) oxalate, bis(1,2-dihydro-2-oxo-1-pyridyl) glyoxal, bis-N-phthalmidyl oxalate, bis(2,4,5 trichloro-6-carbopentoxyphenyl) oxalate, bis(2,4,5-trichloro-6-carbobutoxyphenyl) oxalate, bis(2,4,6-trichlorophenyl) oxalate, and phthalimido 3,6,6-trisulfo-2-naphthyl oxalate. A preferred oxalate would be bis(2-carbopentyloxy-3,5,6-trichlorophenyl) oxalate.

Peroxide reactive compounds also include oxamides. Oxamides suitable for use in the current invention are represented by the following structure:

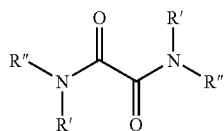

wherein R' is trifluoromethane sulfonyl, 2,4,5-trichlorophenyl, 2,3,4,5,6-pentafluorophenyl, 2,4-dinitrophenyl, phenyl, or other substituted derivatives thereof. Optionally, R' and/or R" may comprise an electron withdrawing group, such as nitro, cyano, carbonyl groups (e.g., aldehydes, ketones, esters, etc.), sulfonyl, trifluoromethyl, and the like. R" is 2,4,5-trichlorophenyl, 2,3,4,5,6-pentafluorophenyl, 2,4-dinitrophenyl, phenyl, or other substituted derivatives thereof. Optionally, R' and/or R" may comprise an electron withdrawing group, such as nitro, cyano, carbonyl groups (e.g., aldehydes, ketones, esters, etc.), sulfonyl, trifluoromethyl, and the like.

Chemiluminescent material 34 preferably includes a dye selected to promote luminescence in a desired spectrum. Suitable dyes include anthracenes and derivatives thereof such as but not limited to benzanthracene, phenanthrene, naphthacene, pentacene, substituted derivatives thereof and the like. Examples of substituents include phenyl, lower alkyl, halide, cyano, alkoxy, and other substituents which do not interfere with the light-emitting reaction described herein. Specific examples of anthracene type compounds include anthracene, diphenylanthracene, or 9,10-bis(phenylethynyl) anthracene. Conjugated fluorescing polymers such as but not limited to poly(phenylene-ethynyl ene), poly(phenylene-vinylene), poly(p-phenylene), polythiophene, substituted derivatives thereof and the like also perform satisfactorily in the current invention. Further, anthracene derivatives covalently bonded to an iptycene, such as the compound provided below, are suitable for use as the dye component of chemiluminescent material 34.

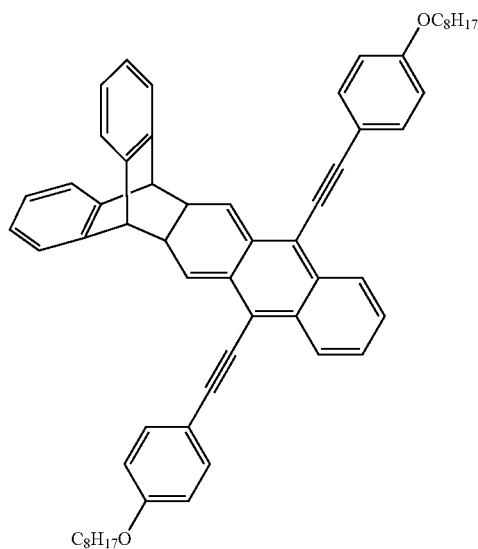

Chemiluminescent material 34 optionally includes a catalyst such as a salt of the conjugate base of a carboxylic acid or a phenol whose original acid has pKa values between 1 and 6 in neat water. A preferred catalyst is sodium salicylate. The catalyst is selected for its ability to improve the reaction rate between chemiluminescent material 34 and the hydrogen peroxide. Other suitable catalysts include but are not limited to: tetrabutylammonium salicylate, potassium salicylate, lithium salicylate, tetrahexylammonium benzoate, benzyltrimethylammonium m-chlorobenzoate, tetraethyl ammonium stearate, calcium stearate, magnesium stearate, lithium stearate, triethylamine, pyridine, piperidine, imidazole, potassium trichlorophenoxide.

Typically, chemiluminescent material 34 is in a solution comprising a solvent exhibiting low or negligible vapor pressure. In the preferred embodiment, the solvent or fluid carrier is a liquid having low volatility. Suitable solvents have boiling points greater than about 300° C. or 400° C. In some cases, the solvent may be a material that remains in the solid state at room temperature (e.g., 25° C.) but undergoes transition to a liquid state at temperatures lower than the operating temperature of detector 10. Thus, chemiluminescent material 34 comprises a light-emitting material such as but not limited to dyes, a peroxide-reactive material, a solvent or other carrier, including fluid carriers or solid-state carriers, and optionally a catalyst.

Solvents suitable for use in the current invention include acyclic or cyclic ethers, such as ethylene glycol ethers, diethyl ether, diamyl ether, diphenyl ether, anisole, tetrahydrofuran, and dioxane, esters such as ethyl acetate, propyl formate, amyl acetate, dialkyl esters of phthalic acid (e.g., dimethyl phthalate, diethyl phthalate, dibutyl phthalate, dioctyl phthalate), methyl formate, triacetin, diethyl oxalate, dioctyl terephthalate, dicyclohexyl phthalate, citric acid esters, methyl benzoate, ethyl benzoate, and butyl benzoate, aromatic hydrocarbons, such as benzene, ethyl benzene, butyl benzene, toluene, and xylene, chlorinated hydrocarbons, such as chlorobenzene, o-dichlorobenzene, m-dichlorobenzene, chloroform, carbon tetrachloride, hexachloroethylene, tetrachlorotetrafluoropropane, and the like. The primary criterion for selecting the solvent is a substance suitable for maintaining the chemiluminescent material 34 in a stable, homogeneous liquid state.

Additionally suitable solvents include ionic liquids. As used herein, the term "ionic liquid" is given its ordinary meaning in the art and refers to a liquid comprising primarily ionic species. That is, at equilibrium, greater than 90% of species in an ionic liquid may be ionic. In some embodiments, greater than 99%, or, greater than 99.9%, of species in an ionic liquid may be ionic. In some cases, the ionic liquid is a salt. Examples of ionic liquids include ethylammonium nitrate and imidazolium salts.

In the preferred embodiment, chemiluminescent material 34 comprises from about 2.5 to about 30.0 percent by weight of a peroxide reactive compound, from about 0.1 to about 1.0 percent by weight of a dye and, optionally, from about 0.0 to about 0.5 percent by weight of a catalyst. The foregoing components being dissolved or dispersed in a suitable solvent as described above.

In particular, the preferred peroxide reactive compound is selected from the following non-limiting group of compounds: bis(2-carbopentyloxy-3,5,6-trichlorophenyl) oxalate, bis(2,4,5 trichloro-6-carbopentoxyphenyl) oxalate, bis(2,4,6-trichlorophenyl) oxalate, bis(pentafluorophenyl) oxalate, and bis(2,4-dinitrophenyl) oxalate. With the most preferred peroxide reactive compound being bis(2,4,5-trichloro-6-carbopentoxyphenyl) oxalate. The preferred dye is 9,10-bis(phenylethynyl)anthracene. If the optional catalyst is included in chemiluminescent material 34, the preferred catalyst is selected from the following non-limiting group of compounds: sodium salicylate, lithium salicylate, and tetrabutylammonium salicylate. With the preferred catalyst being sodium salicylate. However, as previously noted, the preferred embodiment omits the catalyst in favor of heating the sample stream and reaction zone. Thus, in the preferred embodiment of detector 10 heater(s) 42 and/or 44 provide the desired reaction rate. The preferred solvent for forming chemiluminescent material 34 is dioctyl terephthalate.

As noted above, the light-emitting material may be any luminescent material, including dyes, oligomers, polymers, combinations thereof, etc. The light-emitting material may be selected to exhibit certain properties, such as a particular emission wavelength, high quantum yield, and/or compatibility (e.g., solubility) with one or more components of the chemiluminescent material. For example, the light-emitting material may be selected to be soluble with respect to a solvent or other carrier to form mixtures (e.g., solutions) having a high concentration of the light-emitting material, e.g., at least 0.15 weight %, at least 0.25 weight %, or greater. In some embodiments, the light-emitting material may be selected to exhibit a high quantum yield, for example, when present in a solution having a high concentration of light-emitting material. As used herein, the "quantum yield" of a material refers to the total emission produced by the material, i.e., the number of photons emitted per adsorbed photon. For example, the quantum yield of the light-emitting material may refer to the amount of light emission produced (e.g., light output). In some cases, the light-emitting material may have a quantum yield of at least 50%, at least 75%, at least 90%, at least 95%, or, in some cases, at least 99% or greater.

The light-emitting material may also include, for example, conjugated polymers such as poly(arylene)s, poly(phenylene vinylene)s and poly(phenylene ethynylene)s.

In some embodiments, the light-emitting material is a rigid, shape-persistent portion which may improve various properties of the materials including solubility and/or emissive properties of the materials. As used herein, a "shape-persistent portion" of a molecule is a portion having a molecular weight of at least 15 g/mol and having a significant amount of rigid structure, as understood by those of ordinary skill in the art. As used herein, a "rigid" structure means a structure, the ends of which are separated by a distance which cannot change (outside of normal molecule-scale changes in temperature, etc.) without breaking at least one bond, as understood by those of ordinary skill in the art. In some embodiments, the shape-persistent portion has a molecular weight of at least 25, 50, or 100 g/mol. Generally, the shape-persistent portion may not move relative to other portions of the molecule via, for example, rotation about a single bond. For example, in this embodiment the shape-persistent portion comprises an aromatic ring structure fused to a portion of the polymer via two adjacent atoms of the polymer, such that the shape-persistent portion may not rotate relative to the two adjacent atoms of the polymer.

Shape-persistent structures may be provided, for example, by aromatic groups, bridged, bicyclic and polycyclic structures, and the like. For example, an iptycene molecule is a shape-persistent portion. By contrast, a molecule including a cyclic structure such as a benzene ring connected to another portion of the molecule via only a single bond, such as in a biphenyl group, has at least a portion of the molecule that is not shape-persistent, since a benzene ring can rotate about a single bond.

Some examples of shape-persistent portions include planar structures, such as aromatic groups (e.g., benzenes, naphthalenes, pyrenes, etc.). The aromatic groups may be rigidly bonded to (e.g., fused to) the light-emitting material, i.e., the aromatic group is bonded to the light-emitting material via two covalent bonds at adjacent positions on the aromatic ring.

In some cases, the shape-persistent portion includes a non-planar structure, such as a bicyclic or polycyclic structure wherein bridgehead atoms are not positioned adjacent to one another within the molecule. Examples include adamantanes, norbornenes, iptycenes, and the like. In one embodiment, the shape-persistent portion comprises a bicyclic ring system that is non-planar (e.g., an iptycene).

As noted above, iptycene compounds and their derivatives are suitable for use as the light-emitting portion of chemiluminescent material 34. An iptycene typically comprises arene planes fused together via at least one [2.2.2]bicyclooctane moiety. Examples of iptycenes include triptycenes (3 arene planes) and pentiptycenes (5 arene planes). For example, the dye may comprise anthracene covalently bonded to an iptycene. In one embodiment, the dye has the following structure,

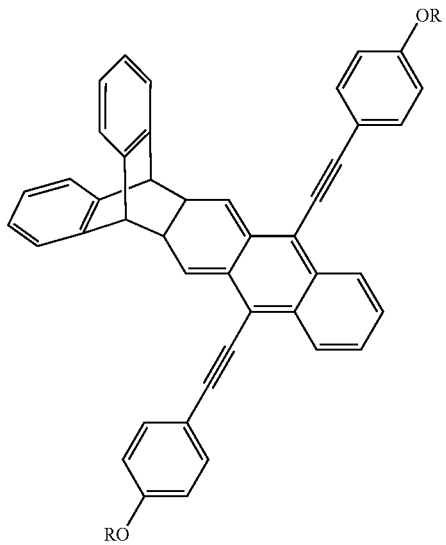

wherein R is alkyl, heteroalkyl, aryl, or heteroaryl.

In some embodiments, the oxalate is preferably treated, prior to use in the chemiluminescent material, to enhance the chemical purity of the oxalate. For example, the oxalate may be obtained commercially and may be recrystallized one or more times to achieve a material having high purity (e.g., greater than 90% pure), as measured by NMR, for use in the chemiluminescent material. In some cases, the oxalate may be recrystallized multiple times (e.g, three times) in hot isopropanol.

In some embodiments, the chemiluminescent material is a liquid chemiluminescent material comprising an oxalate (e.g., bis(2-carbopentyloxy-3,5,6-trichlorophenyl)oxalate (CPPO), oxalic acid bis[2,4,5-trichloro-6-(pentyloxycarbonyl)phenyl]ester), a dye, i.e. the light-emitting component, (e.g., a dye comprising anthracene covalently bonded to an iptycene), and a solvent (e.g., dicyclohexyl phthalate or dioctyl terephthalate). In some cases, the chemiluminescent material may be coated onto a bead-filled capillary, as described herein.

In an illustrative embodiment utilizes an iptycene compound in chemiluminescent material 34, the chemiluminescent material comprises 49.875 weight % CPPO, 0.25 weight % iptycene-containing anthracene dye, and 49.875 weight % dicyclohexyl phthalate.

II. Method for Detecting Vapor-Phase Hydrogen Peroxide

With continued reference to the drawings and the description of detector 10, the current invention also provides improved methods for detecting vapor-phase hydrogen peroxide. In particular, the methods of the current invention are not limited to a laboratory but may be carried out in the field environment such as airport security, sporting events and field checkpoints.

In the methods of the current invention, detector 10 is assembled and prepared for use. For the purposes of this description, assembly is primarily concerned with installation of support 36 carrying chemiluminescent material 34 within sensor assembly 30. Following assembly, tip 40 and reaction zone 50 are heated to the desired operating temperature for the selected chemiluminescent material 34. Heating of tip 40 and reaction zone 50 improves the reaction rate of hydrogen peroxide and chemiluminescent material 34. As indicated above, the preferred temperature may vary depending on the components of chemiluminescent material 34.

Prior to operation of detector 10, pump 14 is turned on and tested to ensure operation within desired parameters. In general, pump 14 provides a gas flow rate of about 20 cm$^3$/min to about 200 cm$^3$/min. In the preferred embodiment, pump 14 permits adjustment of the flow rate to accommodate operational conditions. Preferably, an in-line flow meter (not shown) monitors gas flow through detector 10 and communicates with a microprocessor or other suitable device to maintain a consistent flow of gas through detector 10 by controlling operation of pump 14.

Either a spun coated capillary 37 or capillary 37 containing beads 39 is positioned within detector 10. When the combination of capillary 37 and beads 39 are used, either sintered or unsintered, pump 62 is activated to supply the initial quantity of chemiluminescent material 34 to reaction zone 50 from reservoir 60. Subsequently, during operation pump 62 will be activated from time to time to maintain a sufficient quantity of chemiluminescent material 34 in reaction zone 50 to react with hydrogen peroxide. As discussed above, the initial quantity of chemiluminescent material 34 is typically about 20 μL and subsequent dosing generally occurs about every 15 minutes. Subsequent dosing of chemiluminescent material 34 is generally between about 1 μL to about 4 μL. Preferably, the operator has the option of adjusting this amount based on operating conditions. While the configuration utilizing pump 62 and reservoir 60 may be used with a capillary 37 lacking beads 39, this is not generally preferred.

Following set up of detector 10, testing of a known sample is preferably carried out. Baseline testing allows the operator to test the operation of the sensor assembly to ensure sufficient dosing and functionality of chemiluminescent material 34. In particular, the testing ensures that optical detector 32 is properly aligned with reaction zone 50 and produces a positive response when the test sample reacts with chemiluminescent material 34.

When used in the field, detector 10 is operated by placing tip 40 in the vicinity of an object of interest. For trace detection, tip 40 will preferably be less than 75 mm from the source. With pump 14 operating, a flowing gas stream enters passageway 20 at a rate between about 30 cm$^3$/min and 200 cm$^3$/min. Preferably, the flow rate is about 120 cm$^3$/min. Flow rate through detector 10 is typically dictated by the size of reaction zone 50 with higher flow rates required in larger reaction zones 50.

As the gas passes through tip 40 it is heated. As noted above, tip 40 is generally heated to a temperature between the range of about 25° C. and about 100° C. Preferably, tip 40 is maintained at a temperature of about 65° C. Thus, the gas will preferably be heated to about 60° C. as it flows through tip 40.

The gas subsequently passes through passageway 20 into sensor assembly 30 where it enters reaction zone 50 at a flow rate of between about 20 cm$^3$/min. to about 200 cm$^3$/min. for a capillary having an inner diameter of about 0.5 mm to about 10 mm. Reaction zone 50 is generally heated to a temperature between about 25° C. to about 150° C. Preferably, the temperature of reaction zone 50 will be about 55° C. As previously noted, the preferred operating temperatures for tip 40 and reaction zone 50 will vary with the composition of chemiluminescent material 34.

Within reaction zone 50, vapor-phase hydrogen peroxide present in the gas reacts with the peroxide reactive portion of chemiluminescent material 34. As recognized by those skilled in the art, this reaction produces energy in the form of the emission of a photon. The resulting energy stimulates the fluorescence of the dye such that light energy is emitted in the visible range; however, the current invention should perform satisfactorily with dyes producing light outside the visible spectrum. The resulting emission of light is detected by optical detector 32 which transmits a signal to a display device (not shown) associated with or incorporated into detector 10.

Typical reaction times producing a light response range between about 1 second to about 20 seconds. Preferably, the reaction time is less than five seconds. Additionally, the chemiluminescent material 34 is selected to provide a fast recovery time following a positive test result. In general, chemiluminescent material 34 recovers from a positive test result in about 60 seconds or less, preferably in about ten seconds or less after the exposure to the hydrogen peroxide vapor has ceased. More preferably, the chemiluminescent material 34 recovers and is ready for exposure to another sample within five seconds or less. Finally, detector 10 is operated under conditions of temperature, flow rate and the selected chemiluminescent material 34 which provide a sensitivity such that vapor-phase hydrogen peroxide as low as 10 parts per billion (ppb) is detectible by this method.

Thus, the method of the current invention does not require prior processing of a vapor-phase hydrogen peroxide. Rather, the current invention permits immediate processing of gases suspected of containing vapor-phase hydrogen peroxide. Accordingly, the methods and apparatus of the current invention are well suited to the field environment where rapid testing of suspected materials for trace amounts of hydrogen peroxide is critical.

The current invention has been described predominately with reference to the preferred embodiment of hand held detector 10. However, larger units suitable for stationary monitoring of selected sites such as check-points are also contemplated by this disclosure. Other embodiments of the current invention will be apparent to those skilled in the art from a consideration of this specification and/or practice of the invention disclosed herein. Accordingly, the foregoing specification is considered merely exemplary of the current invention. The true scope of the current invention is defined by the following claims.

The invention claimed is:
1. An apparatus for detecting vapor-phase hydrogen peroxide, said apparatus comprising:
   a housing having a passageway therethrough, said passageway comprising a portion having a non-linear path;
   an inlet for receiving a vapor-phase sample in fluid communication with said passageway;
   an outlet in fluid communication with said passageway;
   a pump in fluid communication with said passageway, said pump suitable for drawing the vapor-phase sample from the exterior of said housing into said passageway;

a sensing assembly arranged within the housing and in fluid communication with said passageway, said sensing assembly comprising a glass capillary comprising a chemiluminescent material, and an optical light detector, said chemiluminescent material having at least component reactive with hydrogen peroxide; and a light-blocking tip arranged within the housing, wherein the light blocking tip comprises the inlet and an air deflector component which forms the non-linear path within the light-blocking tip such that the vapor-phase sample entering the inlet is forced through the non-linear path and ambient light is substantially precluded from contacting the sensing assembly.

2. The apparatus of claim 1, wherein said apparatus further comprises a heater constructed and arranged to heat said tip.

3. The apparatus of claim 1, wherein said sensing assembly further comprises a heater constructed and arranged to heat said chemiluminescent material.

4. The apparatus of claim 1, wherein said sensing assembly further comprises a single heater constructed and arranged to heat said chemiluminescent material and said tip.

5. The apparatus of claim 1, wherein said chemiluminescent material is formed on the interior walls of the glass capillary.

6. The apparatus of claim 5, wherein said chemiluminescent material is formed as a layer having a thickness of about 2 μm to about 10 μm.

7. The apparatus of claim 1, further comprising a plurality of glass beads positioned within the glass capillary, said chemiluminescent material formed on the surface of the glass beads.

8. The apparatus of claim 1, wherein said chemiluminescent material comprises a light-emitting material, a peroxide-reactive material and a carrier.

9. The apparatus of claim 8, wherein said light-emitting compound is selected from the group consisting of: iptycene compounds, anthracenes, diphenylanthracenes, 9,10-bis(phenylethynyl) anthracene, benzanthracenes, phenanthrenes, naphtacenes, pentacenes, poly(arylene)s, poly(phenylene vinylene)s, poly(phenylene ethynylene)s, 5-amino-2, 3-dihydrophthalazine-1,4-dione, 3-aminophthalhydrazide, 2,4,5-triphenylimidazole, 10,10'-dialkyl-9,9'-biacridinium salts, and 9-chlorocarbonyl-10-methylacridinium chloride.

10. The apparatus of claim 8, wherein said peroxide reactive compound is selected from the group consisting of bis(2, 4,6-trichlorophenyl) oxalate, bis(2-carbopentyloxy-3,5,6-trichlorophenyl)oxalate, or oxalic acid bis [2,4,5-trichloro-6-(pentyloxycarbonyl)phenyl]ester, bis(2-nitrophenyl) oxalate, bis(2,4-dinitrophenyl) oxalate, bis(2,6-dichloro-4-nitrophenyl) oxalate, bis(2,4,6-trichlorophenyl) oxalate, bis(3-trifluoromethyl-4-nitrophenyl) oxalate, bis(2-methyl 4,6-dinitrophenyl) oxalate, bis(1,2-dimethyl-4,6-dinitrophenyl) oxalate, bis(2,4-dichlorophenyl) oxalate, bis(2,5-dinitrophenyl) oxalate, bis(2-formyl-4-nitrophenyl) oxalate, bis(pentachlorophenyl) oxalate, bis(pentalluorophenyl) oxalate, bis (1,2-dihydro-2-oxo-l-pyridyl) glyoxal, bis-N-phthalmidyl oxalate, bis(2,4,5 trichloro-6-carbopentoxyphenyl) oxalate, bis(2,4,5-trichloro-6-carbobutoxyphenyl) oxalate, bis(2,4,6-trichlorophenyl) oxalate, and phthalimido 3,6,6-trisulfo-2-naphthyl oxalate.

11. The apparatus of claim 8, wherein said peroxide reactive compound is an oxamide having the following formula

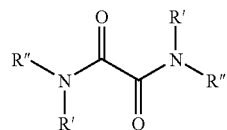

wherein R' is selected from the group consisting of trifluoromethane sulfonyl, 2,4,5-trichlorophenyl, 2,3,4,5,6-pentafluorophenyl, 2,4-dinitrophenyl and phenyl and wherein R" is selected from the group consisting of 2,4,5-trichlorophenyl, 2,3,4,5,6-pentafluorophenyl, 2,4-dinitrophenyl, phenyl.

12. The apparatus of claim 8, wherein said peroxide reactive compound is an oxamide having the following formula

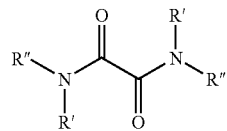

wherein R' is a group comprising an electron withdrawing group, selected from the group consisting of nitro, cyano, carbonyl, sulfonyl and trifluoromethyl and R" is a group comprising an electron withdrawing group, selected from the group consisting of nitro, cyano, carbonyl, sulfonyl and trifluoromethyl.

13. The apparatus of claim 8, wherein said carrier is selected from the group consisting of: ethylene glycol ethers, diethyl ether, diamyl ether, diphenyl ether, anisole, tetrahydrofuran, dioxane, ethyl acetate, propyl formate, amyl acetate, dimethyl phthalate, diethyl phthalate, dibutyl phthalate, dioctyl phthalate, methyl formate, triacetin, diethyl oxalate, dioctyl terphthalate, citric acid ester, methyl benzoate, ethyl benzoate, butyl benzoate, benzene, ethyl benzene, butyl benzene, toluene, xylene, chlorobenzene, o-dichlorobenzene, m-dichlorobenzene, chloroform, carbon tetrachloride, hexachloroethylene, tetrachlorotetrafluoropropane, or combinations thereof.

14. The apparatus of claim 8, wherein said chemiluminescent material further comprises a catalyst is selected from the group consisting of: sodium salicylate, tetrabutylammonium salicylate, potassium salicylate, lithium salicylate, tetrahexylammonium benzoate, benzyltrimethylammonium m-chlorobenzoate, tetraethyl ammonium stearate, calcium stearate, magnesium stearate, lithium stearate, triethylamine, pyridine, piperidine, imidazole, potassium trichlorophenoxide.

15. The apparatus of claim 8, wherein said light-emitting material and said peroxide-reactive material have the same chemical structure.

16. The apparatus of claim 1, wherein the air deflector component includes a C-shaped channel which does not travel through the center of the air deflector component cross-section, the C-shaped channel providing the non-linear path within the light-blocking tip.

* * * * *